United States Patent
Liu et al.

(10) Patent No.: US 8,406,874 B2
(45) Date of Patent: *Mar. 26, 2013

(54) DEFIBRILLATOR WITH A NORMALIZED ELECTRODE INTERFACE AND DEFIBRILLATING ELECTRODE

(75) Inventors: Bin Liu, Shenzhen (CN); Hu Luo, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/572,200

(22) Filed: Aug. 10, 2012

(65) Prior Publication Data

US 2012/0330389 A1    Dec. 27, 2012

Related U.S. Application Data

(63) Continuation of application No. 12/350,749, filed on Jan. 8, 2009, now Pat. No. 8,265,748.

(30) Foreign Application Priority Data

Mar. 13, 2008   (CN) .......................... 2008 1 0065563

(51) Int. Cl.
*A61N 1/34* (2006.01)
(52) U.S. Cl. .................... 607/6; 607/5; 607/7; 607/8
(58) Field of Classification Search .................. 607/2–8, 607/59–62, 115–119
See application file for complete search history.

(56) References Cited

U.S. PATENT DOCUMENTS

| 6,134,468 | A | 10/2000 | Morgan et al. |
| 7,149,576 | B1 * | 12/2006 | Baura et al. .................... 607/6 |
| 7,214,189 | B2 * | 5/2007 | Zdeblick .................... 600/300 |
| 7,747,319 | B2 * | 6/2010 | Freeman .................... 607/6 |
| 2002/0065480 | A1 * | 5/2002 | Hofmann .................... 604/21 |
| 2002/0087195 | A1 | 7/2002 | Hansen |
| 2009/0234403 | A1 | 9/2009 | Liu et al. |

FOREIGN PATENT DOCUMENTS

| CN | 1730126 A | 2/2006 |
| CN | 1859946 A | 11/2006 |

OTHER PUBLICATIONS

Notice of Allowance mailed Jul. 31, 2012 as received in U.S. Appl. No. 12/350,749.
Office Action mailed Apr. 10, 2012 as received in U.S. Appl. No. 12/350,749.
Office Action mailed Oct. 28, 2011 as received in U.S. Appl. No. 12/350,749.

* cited by examiner

*Primary Examiner* — Rex R Holmes
(74) *Attorney, Agent, or Firm* — Kory D. Christensen; Stoel Rives LLP

(57) ABSTRACT

A defibrillator includes a defibrillator mainframe and a defibrillating electrode. The defibrillator mainframe includes a main control unit and a master device electrically connected to the main control unit. The defibrillating electrode comprises a slave device supporting a bus protocol, the master device and slave device being interconnected through a bus.

4 Claims, 3 Drawing Sheets

DEFIBRILLATOR WITH A NORMALIZED ELECTRODE INTERFACE AND DEFIBRILLATING ELECTRODE

CROSS-REFERENCE TO RELATED APPLICATIONS

This application is a continuation of U.S. patent application Ser. No. 12/350,749, filed Jan. 8, 2009, now U.S. Pat. No. 8,265,748, for "DEFIBRILLATOR WITH A NORMALIZED ELECTRODE INTERFACE AND DEFIBRILLATING ELECTRODE," which claims the benefit of Chinese Patent Application No. 200810065563.3, filed Mar. 13, 2008, for "DEFIBRILLATOR WITH A NORMALIZED ELECTRODE INTERFACE AND DEFIBRILLATING ELECTRODE," both of which are incorporated herein by reference.

TECHNICAL FIELD

The present disclosure relates to defibrillators.

SUMMARY

A defibrillator with a normalized electrode interface is disclosed.

DETAILED DESCRIPTION

A defibrillator is a first aid device for restoring the heart beat of a cardiac patient using electrical shock. One component of a defibrillator is a defibrillating electrode that directly contacts a human body for shock defibrillation of a patient under the control of a defibrillator mainframe. There are many kinds of defibrillating electrodes, including, but not limited to, external paddles, internal paddles, and multifunction electrode pads. Adult electrodes differ from child electrodes. Different kinds of electrodes vary significantly in terms of service life and operational characteristics.

At present, defibrillator mainframes have no way of identifying the type of electrode being used. Furthermore, there is no automated way for determining whether electrodes have exceeded their useful life. Hospitals have been maintaining and managing defibrillating electrodes manually. Unfortunately, manual managing of such first aid equipment creates potential risks for high risk patients. Accidents may be caused by possible misusage of electrode types, or use of defibrillating electrodes that have expired or have other problems. The consequences of such mistakes are severe.

Typically, besides discharging cables, a defibrillating electrode is provided with functional keys, such as for charging, discharging, increasing energy, and decreasing energy, as well as several corresponding indicator lights. The defibrillator mainframe needs to obtain key assignment information for the functional keys and control the on/off state of the indicator lights. As a current mode for connecting a defibrillating electrode to a defibrillator mainframe, electrode cables are used to directly interconnect signal wires of keys and indicator lights on the defibrillating electrode with an internal controller of the mainframe.

Figure 1:
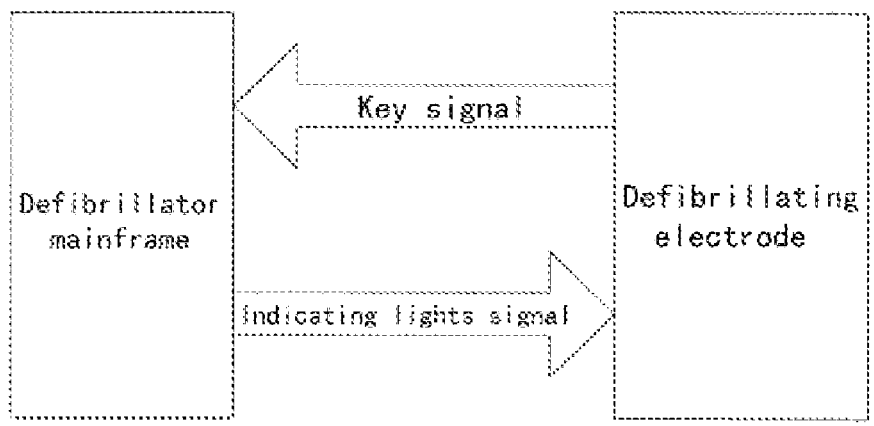
FIG. 1 is a first schematic view of a defibrillator mainframe and a defibrillating electrode.

As shown in FIG. 1, this interconnection and communication mechanism is simple and straightforward, easy to realize without complicated protocols, and has simple hardware. However, this mechanism lacks compatibility and extendibility due to non-normalized electrode interfaces and includes a plurality of interconnecting wires, since each of the functional keys and the indicator lights would require one connecting wire, increasing the cost of the electrode cable.

The present disclosure provides a defibrillator with a normalized electrode interface, which allows fewer connecting wires between a defibrillator mainframe and an electrode and can identify different defibrillating electrodes and perform information interaction therewith.

In one embodiment, a defibrillator comprises a normalized electrode interface including a defibrillator mainframe and a defibrillating electrode. The defibrillator mainframe may include a main control unit and a master device connected to the main control unit. The defibrillating electrode may include a slave device supporting a bus protocol, and the master device and the slave device may be interconnected through a bus.

In one embodiment, the master device is a 1-wire master device, the slave device on the defibrillating electrode is a 1-wire slave device, and the 1-wire master device and the 1-wire slave device are interconnected through a 1-wire bus.

The 1-wire slave device may include a 1-wire control module for controlling indicator lights on the defibrillating electrode and collecting key information from the defibrillating electrode, the 1-wire control module being connected to the 1-wire master device through the 1-wire bus.

The 1-wire slave device may further include a 1-wire storage module, the 1-wire storage module being connected to the 1-wire master device through the 1-wire bus.

The present disclosure also provides a defibrillator with a normalized electrode interface including a main control unit and a master device connected to the main control unit, the master device being connected to an externally connected slave device through a bus.

In one embodiment, the present disclosure provides a defibrillating electrode including an electrode terminal and a slave device supporting a bus protocol, the slave device being connected to a master device through a bus.

In one embodiment, the defibrillator mainframe and the electrode are interconnected by a bus and information interaction is performed therebetween. The defibrillator has a normalized interface, which allows fewer connection wires. Even if the number of keys and indicator lights on the electrodes is increased, the number of connecting wires does not need to be increased. Furthermore, with a bus protocol, different electrodes may be identified, which enables the defibrillator mainframe to identify different electrodes and avoids misusage of electrode types.

In one configuration, a 1-wire bus is used, which allows simpler wire-connection between the defibrillator mainframe and the electrode. According to a 1-wire bus protocol, when adding a 1-wire slave device on the electrode, different electrodes can have a corresponding specific identification, which allows the defibrillator mainframe to identify defibrillating electrodes of different types and different manufacturers.

In one embodiment, the mainframe may control the slave devices on the electrode through the 1-wire bus by adding multiple bus devices with specific functions on the defibrillating electrode and connecting the mainframe of a defibrillating monitor to the slave devices (chips with specific functions and the like) on the electrode through the structure of bus, extending the functionality of the defibrillating electrode. For example, a chip may be added with a control function so that the mainframe may control keys and indicator lights on the electrode. Similarly, chips may be added with a memory function so as to accomplish information storing and reading functions. Thus the defibrillating electrode may have an information tracing and management function so as to prevent defibrillating electrodes that are expired or have problems from being used.

Figure 2:
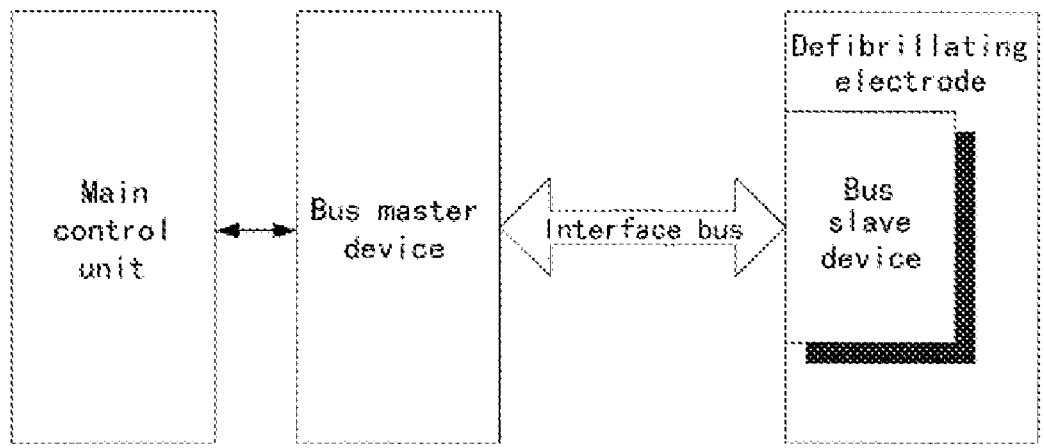
FIG. 2 is a second schematic view of a defibrillator mainframe and a defibrillating electrode.

Referring to FIG. 2, a defibrillator may include a defibrillator mainframe and a defibrillating electrode. In one embodiment, the defibrillator mainframe comprises a main control unit (e.g., a CPU) and a master device connected to the main control unit. The defibrillating electrode may include an electrode terminal (not shown) for supplying high voltage and a slave device supporting a bus protocol. The electrode terminal may be embodied, for example, as a paddle or a pad that obtains a high voltage from the defibrillator mainframe via cables. The master device and the slave device may be connected with a bus through which the defibrillator mainframe performs information interaction with the defibrillating electrode.

An interface bus may serve as the communicating bridge between the defibrillator mainframe and the electrode, and may be a bus structure in any form known by a skilled artisan according to the system requirements. The master device achieves a mainframe function of the bus. In one embodiment, the master device provides control commands via the bus to operate the slave device on the bus, according to protocol requirements of the bus. The master device also resolves data transmitted via the bus from the slave device to learn actions of the slave device. In one embodiment, the defibrillating electrode is equipped with a slave device that supports the interface bus protocol, which can accomplish specific functions, such as sampling key assignments, controlling the on/off status of the indicator lights and storing electrode information, in response to instructions sent by the master device.

Figure 3:
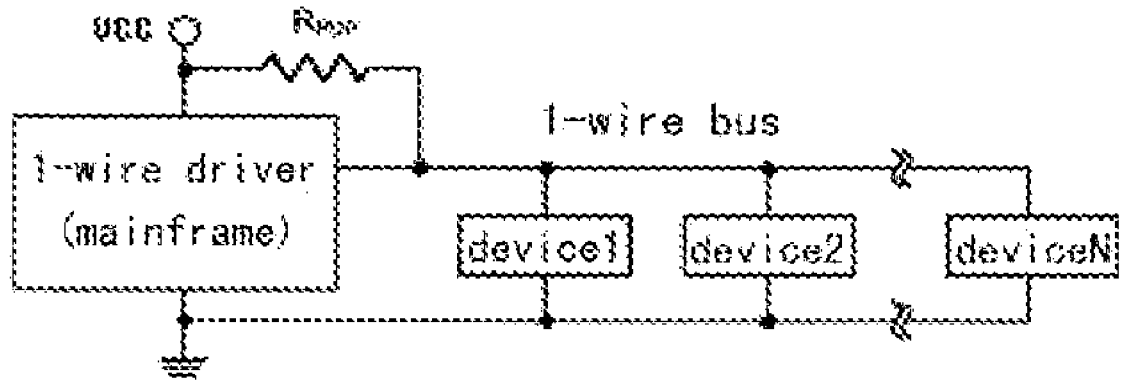
FIG. 3 is a structural block diagram of a 1-wire system.

In one embodiment, a 1-wire protocol is employed as the interface bus protocol. The 1-wire bus is a bus structure with single wire system. As shown in FIG. 3, a typical 1-wire network hardware interface comprises three parts: a 1-wire mainframe, a 1-wire device, and a pull-up resistor. The 1-wire mainframe and the 1-wire device are both connected to the bus by an Open Drain (OD) output structure to ensure that the bus is at a high level state while being idle. In one configuration, the 1-wire device directly obtains operating electric power from the bus for saving power lines. At the same time, a bit-oriented self synchronous data transmission mode enables the 1-wire bus to save clock lines.

In one embodiment, the 1-wire communication protocol includes four basic signalings: reset/response, 1-writing time slot, 0-writing time slot, and reading time slot. There may be a strict time limitation for each signaling. In one embodiment, all other operation instructions that support the 1-wire communication protocol devices may be based on these four signalings. Operational instructions of these devices may be converted into ROM instructions and special function instructions according to their functions.

As specified in the 1-wire protocol, each instruction code may be a piece of eight bit data. In addition, each 1-wire device may have a unique 64-bit ID code, with which a unique ID identification may be configured for the 1-wire slave device of the defibrillating electrode, the unique ID identification being a specific identification of the defibrillating electrode. The ROM instruction is an operating instruction for the 64-bit ID code. The special function instruction is an instruction that is capable of accomplishing a specific function, for example, when reading data at a certain address of a 1-wire memory device (EEPROM), a ReadMemory instruction may be used for accomplishing this function.

First, the bus mainframe may give a ReadMemory instruction and then may provide a two-byte destination address to the 1-wire EEPROM device. Subsequently, the mainframe starts reading data and a CRC that is computed with the instruction code, address, and data from the destination address. These data may all interact with the 1-wire device through reading/writing time slots. Similar instructions may also include an internal register writing instruction (WriteRegister), a temporary storage reading instruction (ReadScratchpad), and the like.

Figure 4:
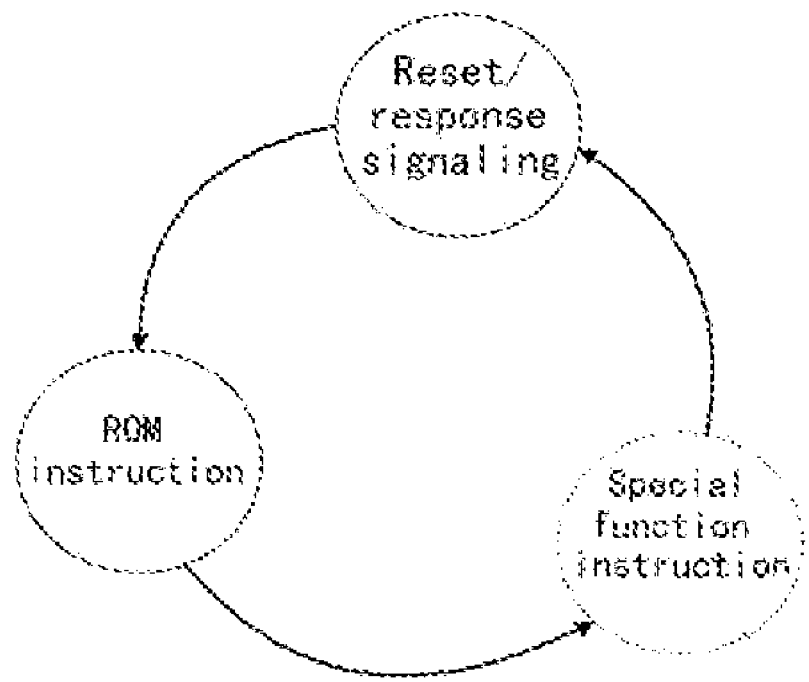
FIG. 4 is an operational flow chart for a 1-wire device.

In one embodiment, the 1-wire protocol also specifies that, after all slave devices on the 1-wire bus are reset (the reset/response signaling is successfully carried out), only when one ROM instruction has been successfully performed can a special function instruction be performed. A flowchart for this process is shown in FIG. 4, which describes steps for a complete 1-wire device operation. In FIG. 4, special function instructions are denoted by a dashed line, which indicates that the special function instructions may not be required for a complete 1-wire operation.

As can be seen, information interaction through the 1-wire bus between the defibrillator mainframe and an electrode allows a normalized interface and fewer connection wires. Even if the number of keys and indicator lights on the electrode is increased, the number of connecting wires does not need to be increased. With the 1-wire protocol, each electrode may have at least one specific identification, which enables the defibrillator mainframe to identify different electrodes and avoids misusage of electrode types.

Figure 5:
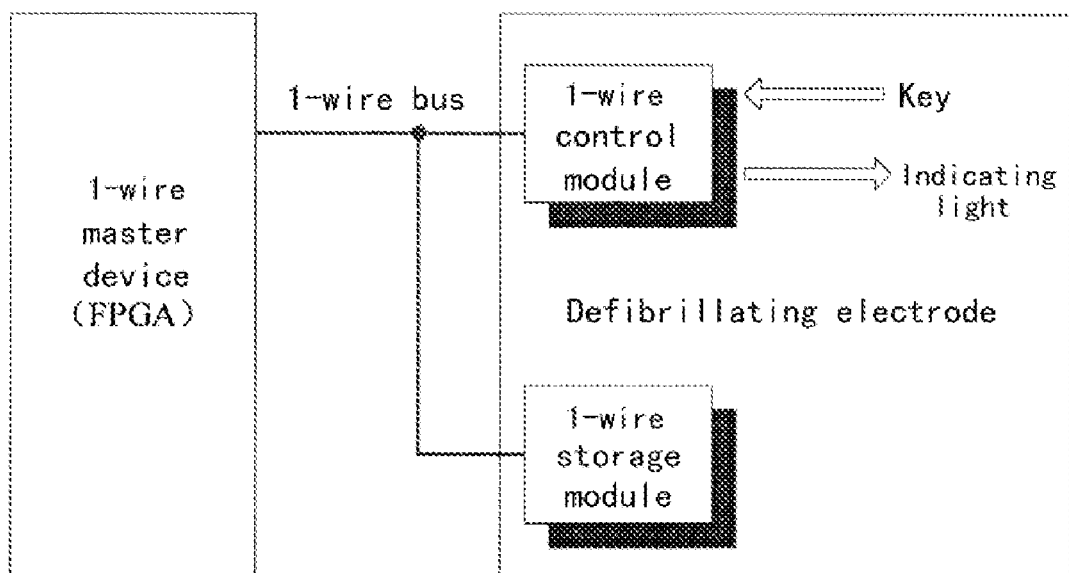
FIG. 5 is a structural schematic view of a 1-wire system.

In the structural diagram of an embodiment shown by FIG. 5, the master device is a 1-wire master device, the slave device is a 1-wire slave device, and the master device and the 1-wire slave device are interconnected through a 1-wire bus. According to selected functions, the 1-wire slave device may comprise different slave devices, for example, a 1-wire control module and a 1-wire storage module. The 1-wire control module may be used to control indicator lights on the defibrillating electrode and sampling key assignment information of the defibrillating electrode. The 1-wire control module and the 1-wire storage module maybe connected to the 1-wire master device through a 1-wire bus, respectively. By adding a chip with control functions, the mainframe may control the keys and indicator lights on the electrode, and by adding a chip with a storage function, information storage and reading functions may be accomplished, thereby a trace management function, so as to prevent defibrillating electrodes that are expired or have problems from being used. The mainframe may interact with the 1-wire slave devices on the electrode through the 1-wire bus by adding multiples of 1-wire devices with specific functions on the defibrillating electrode and connecting the mainframe of a defibrillating monitor to the 1-wire slave devices on the electrode (chips with specific functions and the like) through the structure of 1-wire bus, extending the functionality of the defibrillating electrode.

In this embodiment, a 1-wire slave device comprising a 1-wire chip with I/O control functionality and a 1-wire chip with storage functionality is configured on the defibrillating electrode. The chip with I/O control functionality functions as a 1-wire control module for realizing the basic function of the defibrillating electrode, that is, controlling keys and indicator lights (LEDs) on the defibrillating electrode. The chip with the storage functionality functions as a 1-wire storage module with a built-in EEPROM. With the storage function of the EEPROM, the electrode may store key assignments and key pressing timings made by a doctor in case of each defibrillation, and at the same time the defibrillator mainframe may also trace the condition of the current electrode by reading the EEPROM upon being powered on. In one embodiment, the chip with control functionality has a plurality of I/O pins directly connected to the keys and LEDs on the electrode.

States of the I/O pins connected to the keys directly reflect the states of the keys and the 1-wire master device reads states (key assignments) of these I/O pins through the 1-wire bus at specified intervals (for example 5 ms) and conduct proper processing on the read key assignments. When a key is pressed, the 1-wire master device may detect changes of key assignments transmitted from the 1-wire control module through the 1-wire bus.

In one embodiment, when a key assignment is considered valid, the 1-wire master device may record the key assignment and current timing, transmit this latched key assignment to the main control unit through an interface connected to the main control unit, and write these data to the 1-wire storage module (EEPROM) through the 1-wire bus. Similarly, the LEDs are turned on/off by changing states of I/O pins connected to the LEDs. When the main control unit needs to change a state of an LED, it gives an instruction to the 1-wire master device. Subsequently, the 1-wire master device operates the 1-wire control module on the electrode through the 1-wire bus according to the instruction. The 1-wire control module changes the level state of the corresponding I/O pin according to the operation of the 1-wire master device so as to realize on/off control of the LED.

Figure 6:
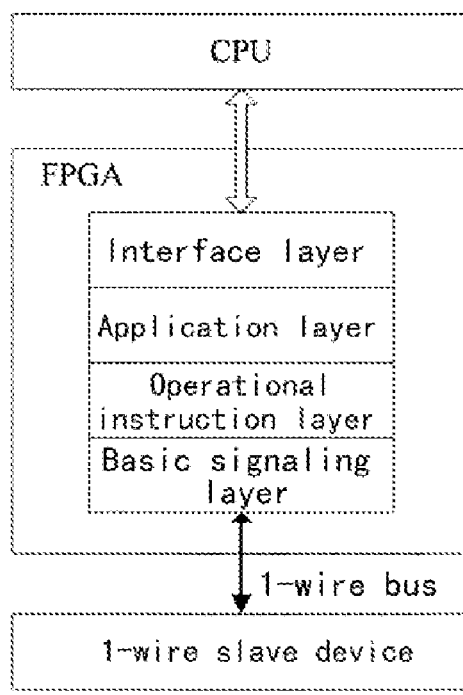
FIG. 6 is a logical block diagram of an implementation of a 1-wire master device with an FPGA.

In this embodiment, the logic function of a field programmable gate array (FPGA) is used to realize the master device functions of the 1-wire bus. The FPGA logic realizes various layers of 1-wire instructions for operational requirements of specific 1-wire slave devices on the defibrillating electrode. The structure of the logic is shown in FIG. 6, wherein the middle area marked by "FPGA" indicates the 1-wire functional module of the FPGA. The logic of the FPGA is accomplished in a layered pattern and each functional module respectively encapsulates instructions of different layers for the 1-wire protocol.

In one embodiment, the basic signaling layer is a basis of the entire logic, the lowest layer logic for directly interacting with the 1-wire device, i.e. realizing the above-mentioned four basic signalings. The operational instruction layer is a logic encapsulation for a single instruction (including the ROM instruction and the special function instruction) in the 1-wire protocol, which realizes various instructions with specific functions by using the basic signaling layer and is a functional module as a bridge among the logics. The operational instruction layer converts parallel data from an upper layer logic to a bit stream complying with the 1-wire protocol and delivers them to the basic signaling layer. The operational instruction layer receives the bit stream transmitted from the basic signaling layer and converts them into parallel data available for the upper layer.

The application layer is a logic module for encapsulating a complete operation process shown in FIG. 4. The interface layer is a logic module for exchanging data with a CPU at an upper layer, and through the interface layer, an application program of the defibrillating monitor system accomplishes operational control for the defibrillating electrode. For example, if the mainframe application program of the defibrillating monitor needs to know the last use condition of the defibrillating electrode connected to the mainframe, it needs to transmit a "use information reading" command through the bus via which the CPU interfaces with the FPGA, the command being decoded by the interface layer and then forwarded to the application layer.

In one embodiment, the application layer starts to perform the corresponding operation process shown in FIG. 4 according to the received command information, and in each stage of the process, the operational instruction layer and the basic signaling layer are activated to work. First, all devices on the 1-wire bus are reset. Thereafter, a ROM instruction is performed to determine a 1-wire slave device (EEPROM device) to be operated. Finally, a ReadMemory instruction is performed to read data information at a corresponding address. After being processed by different layers of logic modules, the data information is transmitted to the CPU application program at the top layer.

In the above embodiments, in addition to the 1-wire chip, other types of 1-wire devices, such as devices accomplishing same functions and supporting the 1-wire protocol, simulated with processors or programmable logic devices, may also be adopted as the 1-wire slave device. The master device may also be implemented in other ways that could provide same functions, e.g., a 1-wire host interface simulated with I/O of a processor or carried on the processor itself, or special 1-wire mainframe control chip externally connected to the CPU and FPGA. Other types of buses, such as a UART bus, an I$^2$C bus, or self-defined bus, may also be used for the bus interface, and the master device on the defibrillator mainframe and the slave devices on the defibrillating electrode may also adopt devices supporting the bus accordingly.

It should be recognized that the embodiments described herein with respect to the figures are meant to be illustrative only and should not be taken as limiting the scope of disclosure. Those of skill in the art will recognize that the illustrated embodiments can be modified in arrangement and detail without departing from the scope of the disclosure. Therefore, the disclosure as described herein contemplates all such embodiments as may be within the scope of the present disclosure.

What is claimed is:

1. A defibrillating electrode comprising:
    an electrode terminal; and
    a slave device supporting a bus protocol, the slave device being connected to a master device through a single wire bus;
    wherein the slave device further comprises a 1-wire storage module, the 1-wire storage module being connected to the master device through the single wire bus; and
    wherein the 1-wire storage module stores electrode expiration and condition information for use by a trace management function that prevents expired or damaged electrodes from being used.

2. The defibrillating electrode according to claim 1, wherein the master device is a 1-wire master device.

3. The defibrillating electrode according to claim 1, wherein the slave device on the defibrillating electrode is a 1-wire slave device.

4. The defibrillating electrode according to claim 3, wherein the 1-wire slave device comprises a 1-wire control module for controlling one or more indicator lights on the defibrillating electrode and collecting key information, the 1-wire control module being connected to the master device through the single wire bus.

* * * * *